United States Patent [19]

Denzel et al.

[11] 4,269,836

[45] May 26, 1981

[54] 4H-PYRAZOLO[4',3':5,6]PYRIDO[4,3-D][1,2,4]TRIAZOLO[3,2-B]-PYRIMIDIN-5(8H)ONE AND DERIVATIVES THEREOF

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 704,855

[22] Filed: Jul. 13, 1976

[51] Int. Cl.³ ............... A61K 31/505; C07D 487/22; C07D 265/30; C07D 279/12

[52] U.S. Cl. ............... 424/246; 544/60; 544/115; 544/247; 424/248.57; 424/251

[58] Field of Search ............... 260/256.4 F, 243 B, 260/247.5 C; 424/251, 248.57, 246; 544/247, 60, 115

Primary Examiner—Donald G. Daus
Assistant Examiner—D. B. Springer
Attorney, Agent, or Firm—Lawrence S. Levinson

[57] ABSTRACT

New 4H-pyrazolo[4',3':5,6]pyrido[3,4-e][1,2,4]triazolo[1,5-a]pyrimidin-5(8H)one and new derivatives thereof have the general formula

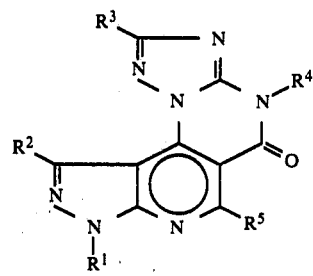

The compounds are useful as anti-inflammatory agents and central nervous system depressants.

18 Claims, No Drawings

4H-PYRAZOLO[4',3':5,6]PYRIDO[4,3-D][1,2,4]TRIAZOLO[3,2-B]-PYRIMIDIN-5(8H)ONE AND DERIVATIVES THEREOF

SUMMARY OF THE INVENTION

This invention relates to the new compounds 4H-pyrazolo[4',3':5,6]pyrido[3,4-e][1,2,4]triazolo[1,5-a]-pyrimidin-5(8H)-one and derivatives thereof. These new compounds have the general formula

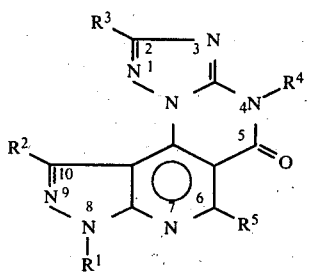

$R^1$ is hydrogen, lower alkyl, phenyl, phenyl-lower alklene, benzoyl or substituted benzoyl.
$R^2$ is hydrogen or lower alkyl.
$R^3$ is hydrogen, lower alkyl, phenyl, lower alkylthio or lower alkylsulfinyl.
$R^4$ is hydrogen, lower alkyl, phenyl-lower alkylene, benzoyl or substituted benzoyl, lower alkanoyl, lower alkoxy-lower alkylene, lower alkylthio-lower alkylene, phenyl or substituted phenyl, amino-lower alkylene or di-lower alkylamino-lower alkylene. The basic amino group may also form one of the heterocycles piperidine, morpholine, thiamorpholine or piperazine.
$R^5$ is hydrogen or lower alkyl.

DETAILED DESCRIPTION OF THE INVENTION

The various groups represented by the symbols are of the following types:

The lower alkyl groups are straight or branched chain hydrocarbon groups having up to seven carbon atoms like methyl, ethyl, propyl, isopropyl, butyl, isobutyl, t-butyl, pentyl and the like. The lower alkylene groups are divalent radicals of the same kind. Examples of the phenyl-lower alkylene groups are benzyl, phenethyl, phenylisopropyl and the like. The $C_1$–$C_4$ and especially the $C_1$–$C_2$ lower alkyl and lower alkylene groups are preferred. The lower alkoxy, lower alkylthio and lower alkylsulfinyl groups have similar alkyl groups attached to the oxygen, sulfur or sulfinyl (SO) group, respectively. The same preferences as to number of carbons apply.

The substituted phenyl and substituted benzoyl groups (i.e., $R_8$-phenyl, $R_8$-benzoyl) are simply substituted benzoyl groups having halogen (the four common halogens, but preferably chlorine or bromine), lower alkyl or lower alkoxy (similar to the lower alkyl groups defined above) groups ($R_8$) on the phenyl ring, for example, p-chlorophenyl, o-chlorophenyl, p-bromophenyl, m-chlorophenyl, m-bromophenyl, p-tolyl, o-tolyl, o-ethylphenyl, p-methoxyphenyl, p-chlorobenzyl, o-chlorobenzyl, p-bromobenzoyl, m-bromobenzoyl, p-methylbenzoyl, o-ethylbenzoyl, p-methoxybenzoyl and the like. Chlorine, bromine and methyl are the preferred substituents in both instances, but unsubstituted phenyl and benzoyl are preferred over the substituted radicals.

The lower alkanoyl groups are the acyl groups of the lower ($C_2$–$C_7$) fatty acids, e.g., acetyl, propionyl, butyryl, isobutyryl and the like. Those with up to four carbons in the chain are preferred, especially acetyl.

The lower alkoxy-lower alkylene and lower alkylthio-lower alkylene groups represented by $R^4$ have radicals like those described above including such groups as methoxymethylene, ethoxymethylene, methoxyethylene, methylthiomethylene, methylthioethylene, ethylthiomethylene, ethylthioethylene, etc.

The amino-lower alkylene groups are of the same type, e.g., aminomethyl, aminoethyl, etc. The di-lower alkylamino-lower alkylene groups are also of the same type wherein the nitrogen is substituted with two lower alkyl groups. In addition, the two lower alkyl groups may join in forming a heterocycle which may include an additional hetero atom. In other words, the di-lower alkylamino-lower alkylene group can take the form

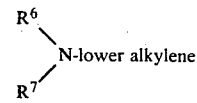

wherein $R^6$ and $R^7$ are lower alkyl groups or join together to complete the heterocycle piperidine, morpholine, piperazine or thiamorpholine (preferably the first three and especially the first two). Preferably the lower alkyl and lower alkylene groups have up to 4 and especially 1 to 2 carbons. Thus, groups like dimethylaminomethyl, diethylaminomethyl, dimethylaminoethyl, diethylaminoethyl, dimethylaminopropyl, piperidinomethyl, piperidinoethyl, morpholinomethyl, morpholinoethyl, thiamorpholinomethyl, thiamorpholinoethyl, piperazinomethyl, piperazinoethyl, piperazinopropyl are included.

Preferably $R^1$ is lower alkyl, especially ethyl; $R^2$ is hydrogen or lower alkyl, especially hydrogen; $R^3$ is hydrogen, lower alkyl, especially methyl, lower alkythio, especially methylthio, or lower alkylsulfinyl, especially methylsulfinyl, with especial preference for hydrogen or lower alkyl; $R^4$ is hydrogen, lower alkyl, especially methyl, ethyl and isopentyl, or di-lower alkylamino-lower alkylene, especially dimethylaminopropyl and dimethylaminoethyl; $R^5$ is lower alkyl or hydrogen, especially hydrogen.

The products of the examples are representative of the various compounds of this invention and constitute especially preferred embodiments.

The new compounds of formula I are formed by the following series of reactions. The symbols in the structural formulas have the same meaning as previously described.

A pyrazolo[3,4-b]pyridine of the formula

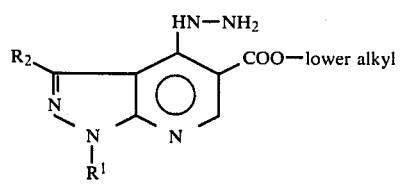

(produced according to the procedure given in U.S. Pat. No. 3,761,487, Sept. 25, 1973) is made to react with a lower alkoxymethylene cyanamide of the formula

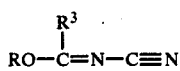
(III)

or a lower alkylthiomethylene cyanamide of the formula

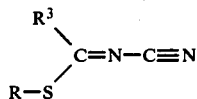
(IV)

wherein R in both formulas is lower alkyl, in an organic solvent like alcohol, or the like.

By this reaction a compound of formula I wherein $R^4$ is hydrogen is obtained.

Compounds of formula I, wherein $R^4$ is other than hydrogen, are obtained by treatment of the compound of formula I wherein $R^4$ is hydrogen, obtained as just described, with the halide $R^4$-hal, wherein hal is a halogen, preferably chlorine or bromine, and $R^4$ has the meaning defined above, in the presence of a base, preferably a base of an alkali metal, like sodium hydride, sodium or potassium alcoholate, like sodium or potassium methoxide or ethoxide, sodium or potassium hydroxide, or the like, in a solvent like diethyleneglycol dimethyl ether.

Compounds of formula I, wherein $R^3$ is lower alkylsulfinyl are obtained from the corresponding compound of formula I wherein $R^3$ is lower alkylthio by oxidizing the latter, e.g., with an alkali metal periodate like sodium metaperiodate.

Additional experimental details are found in the examples.

The new compounds of this invention have central nervous sytem depressant activity and can be used as psychotropic agents, e.g., as ataractic agents for the relief of anxiety and tension states, for example, in mice, cats, rats, dogs and other mammalian species. For this purpose a compound or mixture of compounds of formula I is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 2 to 15 mg. per kilogram per day, is appropriate.

The new compounds of this invention also have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carrageenan edema or delayed hypersensitivity skin reaction tests in rats.

The compounds of the invention can be utilized by formulation in compositions such as tablets, capsules or elixirs for oral administration or in sterile solutions or suspensions for parenteral administration. About 10 to 250 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor.

For topical administration as an anti-inflammatory agent, a conventional lotion, ointment or cream containing about 0.1 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

8-Ethyl-4H-pyrazolo[4',3':5,6]pyrido[3,4-e][1,2,4]triazolo[1,5-a]-pyrimidin-5(8H)one 249 g. of 1-ethyl-4-hydrazino-1H-pyrazolo[3,4-b]pyridine-5-carboxylic acid, ethyl ester (1 mol.) are refluxed in 1.5 liters of dry dioxane together with 98 g. of ethoxymethylene cyanamide for 12 hours. After cooling to room temperature, the precipitated 8-ethyl-4H-pyrazolo[4',3':5,6]pyrido[3,4-e][1,2,4]triazolo[1,5-a]pyrimidin-5(8H)-one is filtered off and recrystallized from dimethylformamide, yield 135 g. (53%); m.p. 355°–356°.

EXAMPLE 2

4-[3-(Dimethylamino)propyl]-8-ethyl-4H-pyrazolo[4',3':5,6]pyrido[3,4-e][1,2,4]triazolo[1,5-a]pyrimidin-5(8H)-one 5.1 g. of 8-ethyl-4H-pyrazolo[4',3':5,6]pyrido[3,4-e][1,2,4]triazolo[1,5-a]pyrimidin-5(8H)-one (0.02 mol.) obtained in Example 1 are treated with 0.6 g. of sodium hydride in 50 ml. of diethylene glycol dimethyl ether at 150° for 1 hour. After this time, the temperature is lowered to about 90° and 3.6 g. of 3-(dimethylamino)propyl chloride are added and heating is continued for 12 hours with stirring. The precipitated inorganic salt is filtered off and the filtrate evaporated to dryness. The remaining 4-[3-(dimethylamino)propyl]-8-ethyl-4H-pyrazolo[4',3':5,6]pyrido[3,4-e][1,2,4]triazolo[1,5-a]pyrimidin-5(8H)- one is recrystallized from butanol, yield 4.5 g. (66%); m.p. 175°–177°.

EXAMPLE 3

8-Ethyl-4-(3-methylbutyl)-4H-pyrazolo[4',3':5,6-]pyrido[3,4-e][1,2,4]triazolo[1,5-a]pyrimidin-5(8H)-one 2.6 g. of 8-ethyl-4H-pyrazolo[4',3':5,6]pyrido[3,4-e][1,2,4]triazolo[1,5-a]pyrimidin-5(8H)-one obtained as in Example 1 (0.01 mol.) are treated with 1 g. of sodium ethoxide in 50 ml. of diethyleneglycoldimethyl ether at 120° for 2 hours. After this time, 2 g. of 3-methyl-1-bromobutane are added and heating is continued for 12 hours at the same temperature with continuous stirring. The inorganic precipitate is filtered off and the mother liquor evaporated to dryness. The remaining 8-ethyl-4-(3-methylbutyl)-4H-pyrazolo[4',3':5,6]-pyrido[3,4-e][1,2,4]triazolo[1,5-a]pyrimidin-5(8H)-one is recrystallized from alcohol, yield 2.1 g. (64%); m.p. 175°–177°.

EXAMPLE 4

8-Ethyl-4-methyl-4H-pyrazolo[4',3':5,6]pyrido[3,4-e][1,2,4]triazolo[1,5-a]pyrimidin-5(8H)-one 2.6 g. of 8-ethyl-4H-pyrazolo[4',3':5,6]pyrido[3,4-e][1,2,4]triazolo[1,5-a]pyrimidin-5(8H)-one (0.01 mol.) are treated with 0.3 g. of sodium in 50 ml. of diethyleneglycol dimethyl ether at reflux temperature with stirring for 30 minutes. After this time, the temperature is lowered to 60° and 3 g. of methyl iodide are added. Stirring and heating is continued for 12 hours. The precipitate of sodium iodide is filtered off and the solvent distilled from the mother liquor. The remaining 8ethyl-4-methyl-4Hpyrazolo[4',3':5,6]pyrido[3,4-e][1,2,4]triazolo[1,5-a]pyrimidin5(8H)-one is recrystallized from butanol, yield 2 g. (75%); m.p. 208°–210°.

EXAMPLE 5

8-Ethyl-2-methylthio-4H-pyrazolo[4',3':5,6]pyrido[3,4-e][1,2,4]triazolo[1,5-a]pyrimidin-5(8H)-one 249 g. of 1-ethyl-4-hydrazino-1H-pyrazolo[3,4-b]pyridine5-carboxylic acid, ethyl ester (1 mol.) are refluxed in 2 liters of butyl alcohol with 114 g. of dimercaptomethylmethylene cyanamide for 10 hours. The solution is cooled to room temperature and the precipitated 8-ethyl-2-methylthio-4Hpyrazolo[4',3':5,6-]pyrido[3,4-e][1,2,4]triazolo[1,5-a]pyrimidin-5(8H)-one is filtered off, yield 140 g. (46%); m.p. >300° (DMF).

EXAMPLE 6

8-Ethyl-2-methylsulfinyl-4H-pyrazolo[4',3'-5,6]pyrido[3,4-e][1,2,4]triazolo[1,5-a]pyrimidin-5(8H)-one 3.01 g. of 8-ethyl-2-methylthio-4H-pyrazolo[4',3':5,6]-pyrido[3,4-e][1,2,4]triazolo[1,5-a]pyrimidin-5(8H)-one obtained in Example 5 are oxidized with 2.2 g. of sodium metaperiodate in aqueous alcohol for 7 days at room temperature. The precipitate of 8-ethyl-2-methylsulfinyl-4H-pyrazolo[4',3':5,6-]pyrido[3,4-e][1,2,4]triazolo[1,5-a]pyrimidin-5(8H)-one is filtered off, washed with water and recrystallized from dimethylformamide, yield 2.8 g. (88%); m.p.>300°.

EXAMPLE 7

4,8-Diethyl-4H-pyrazolo[4',3':5,6]pyrido[3,4-e][1,2,4]triazolo[1,5-a]pyrimidin-5(8H)-one By substituting ethyl iodide for the methyl iodide in the procedure of Example 4, 4,8-dimethyl-4H-pyrazolo[4',3':5,6]-pyrido[3,4-e][1,2,4]triazolo[1,5-a]pyrimidin-5(8H)-one is obtained.

EXAMPLE 8

8-Ethyl-4-(2-morpholino)ethyl-4H-pyrazolo[4',3':5,6-]pyrido[3,4-e][1,2,4]triazolo[1,5-a]pyrimidin-5(8H)-one 2.7 g. of 8-ethyl-4H-pyrazolo[4',3':5,6]pyrido[3,4-e][1,2,4]triazolo[1,5-a]pyrimidin-5(8H)-one (0.01 mol.) and 0.3 g. of sodium are refluxed for one hour in 30 ml. of diethyleneglycol dimethylether with stirring. The temperature is lowered to 90° and 2 g. of 1-chloro-2-morphoninoethane are added and stirring is continued for 24 hours. The inorganic precipitte is filtered off, the solvent removed in vacuo to obtain the product, 8-ethyl-4-(2-morpholino)ethyl-4H-pyrazolo[4',3':5,6-]pyrido[3,4-e][1,2,4]triazolo[1,5-a]pyrimidin-5(8H)-one.

EXAMPLE 9

8-Ethyl-4-(2-piperidino)ethyl-4H-pyrazolo[4',3':5,6-]pyrido[3,4-e][1,2,4]triazolo[1,5-a]pyrimidin-5(8H)-one By substituting for the 3-(dimethylamino)propyl chloride in Example 2 the equivalent amount of 1-chloro-2-piperidinoethane, 8-ethyl-4-(2-piperidino)ethyl-4H-pyrazolo[4',3':5,6]pyrido[3,4-e][1,2,4]triazolo[1,5-a]pyrimidin-5(8H)-one is obtained.

EXAMPLE 10

4-[2-(Diethylamino)ethyl]-8-ethyl-4H-pyrazolo[4',3,:5,6]pyrido[3,4-e][1,2,4]triazolo[1,5-a]pyrimidin-5(8H)-one By substituting for the 3-(dimethylamino)propyl chloride in Example 2 the equivalent amount of 1-chloro-2-diethylaminoethane, 4-[2-(diethylamino)ethyl]-8-ethyl-4H-pyrazolo[4',3':5,6]pyrido [3,4-e][1,2,4]triazolo[1,5-a]pyrimidin-5(8H)-one is obtained.

EXAMPLE 11

4-Methyl-4H-pyrazolo[4',3':5,6]pyrido[3,4-e][1,2,4]triazolo[1,5-a]pyrimidin-5(8H)-one By substituting an equivalent amount of 4-hydrazino1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 then continuing as in Example 4, 4H-pyrazolo[4',3':5,6]pyrido[3,4-e][1,2,4]triazolo[1,5-a]pyrimidin-5(8H)-one and 4-methyl4H-pyrazolo[4',3':5,6]pyrido[3,4-e][1,2,4]triazolo[1,5-a]pyrimidin-5(8H)-one, respectively, are obtained.

EXAMPLE 12

4-Butyl-8-ethyl-4H-pyrazolo[4'3,':5,6]pyrido[3,4-e][1,2,4]triazolo[1,5-a]pyrimidin-5(8H)-one By substituting butyl iodide for the methyl iodide in the procedure of Example 4, 4-butyl-8-ethyl-4H-pyrazolo[4',3':5,6]pyrido [3,4-e][1,2,4]triazolo[1,5-a]pyrimidin-5(8H)-one is obtained.

EXAMPLE 13

4-Phenylmethyl-4H-pyrazolo[4',3':5,6]pyrido[3,4-e][1,2,4]triazolo[1,5-a]pyrimidin-5(8H)-one By substituting the 4H-pyrazolo[4',3':5,6]pyrido[3,4-e][1,2,4]triazolo[1,5-a]pyrimidin-5(8H)-one of Example 11 for the 8-ethyl -4H-pyrazolo[4',3':5,6]pyrido[3,4-e][1,2,4]-triazolo[1,5-a]pyrimidin-5(8H)-one and benzyl iodide for the methyl iodide in the procedure of Example 4, 4-phenylmethyl4H-pyrazolo[4',3':5,6]pyrido[3,4-e][1,2,4]triazolo[1,5-a]pyrimidin-5(8H)-one is obtained.

EXAMPLE 14

8-Ethyl-4phenylethyl-4H-pyrazolo[4',3':5,6]pyrido[3,4-e][1,2,4]triazolo[15-a]pyrimidin-5(8H)-one By substituting phenylethyl bromide for the methyl iodide in the procedure of Example 4,8-ethyl-4-phenylethyl4H-pyrazolo[4',3':5,6]pyrido[3,4-e][1,2,4]triazolo[1,5-a]pyrimidin-5(8H)-one is obtained.

EXAMPLE 15

4,8,10-Trimethyl-4H-pyrazolo[4',3':5,6]pyrido[3,4-e][1,2,4]triazolo[1,5-a]pyrimidin-5(8H)-one By substituting 1,3-dimethyl-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 and proceeding as in Example 4, 8,10-dimethyl-4H-pyrazolo[4',3':5,6]pyrido[3,4-e][1,2,4]triazolo[1,5-a]pyrimidin5(8H)-one and 4,8,10-trimethyl-4H-pyrazolo[4',3':5,6]pyrido[3,4-e][1,2,4]triazolo[1,5-a]pyrimidin-5(8H)-one are obtained.

EXAMPLE 16

2-Ethyl-8-isopropyl-4-propionyl-4H-pyrazolo[4',3':5,6-]pyrido[3,4-e][1,2,4]triazolo[1,5-a]pyrimidin-5(8H)-one By substituting 1-isopropyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester and 1-ethoxypropylidene cyanamide for the ethoxymethylene cyanamdie in the procedure of Example 1, and then proceeding as in Example 4 but substituting propionyl bromide for the methyl iodide, 2-ethyl-8-isopropyl-4H-pyrazolo[4',3':5,6]pyrido[3,4-e][1,2,4]triazolo[1,5-a]-pyrimidin-5(8H)-one and 2-ethyl-8-isopropyl-4-propionyl4H-pyrazolo[4', 3':5,6]pyrido[3,4-e][1,2,4]triazolo[1,5-a]pyrimidin-5(8H)-one, respectively, are obtained.

EXAMPLE 17

4-(4-Chlorobenzoyl)-10-ethyl-4H-pyrazolo[4',3':5,6-]pyrido[3,4-e] [1,2,4]triazolo[1,5-a]pyrimidin-5(8H)-one By substituting 4-hydrazino-3-ethyl-1H-pyrazolo[3,4-b]pyridine-5-carboxylic acid propyl ester for the 1-ethyl-4-hydrazino-1H-pyrazolo[3,4-b]pyridine-5-carboxylic acid, ethyl ester in the procedure of Example 1, and then substituting 4-chlorobenzoyl bromide for the methyl iodide in the procedure of Example 4, 10-ethyl-4H-pyrazolo[4',3':5,6]-pyrido[3,4-e][1,2,4]triazolo[1,5-a]pyrimidin-5(8H)-one and 4-(4-chlorobenzoyl)-10-ethyl-4H-pyrazolo[4',3':5,6]pyrido[3,4-e][1,2,4]triazolo[1,5-a]pyrimidin-5(8H)-one, respectively, are obtained.

EXAMPLE 18

4-Benzoyl-8-phenyl-4H-pyrazolo[4',3':5,6]pyrido[3,4-e][1,2,4]triazolo[1,5-a]pyrimidin-5(8H)-one By substituting 4-hydrazino-1-phenyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, then proceeding as in Example 4 but substituting benzoyl iodide for the methyl iodide, 8-phenyl-4H-pyrazolo[4',3':5,6]-pyrido[3,4-e][1,2,4]triazolo[1,5-a]pyrimidin-5(8H)-one and 4-benzoyl-8-phenyl-4H-pyrazolo[4',3':5,6]pyrido[3,4-e][1,2,4]triazolo[1,5-a]pyrimidin-5(8H)-one, respectively, are obtained.

EXAMPLE 19

4,6-Dimethyl-8-ethyl-4H-pyrazolo[4',3':5,6]pyrido[3,4-e][1,2,4]triazolo[1,5-a]pyrimidin-5(8H)-one By substituting 1-ethyl-4-hydrazino-6-methyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, then proceeding as in Example 4, 8-ethyl-6-methyl-4H-pyrazolo[4',3':5,6]pyrido[3,4-e][1,2,4]triazolo[1,5-a]pyrimidin-5(8H)one and 4,6-dimethyl-8-ethyl-4H-pyrazolo[4',3':5,6]pyrido[3,4-e][1,2,4]triazolo[1,5-a]pyrimidin-5(8H)-one, respectively, are obtained.

EXAMPLE 20

8-Benzyl-4-(3-methylbutyl)-4H-pyrazolo[4',3':5,6-]pyrido[3,4-e][1,2,4]triazolo[1,5-a]pyrimidin-5(8H)-one By substituting 1-benzyl-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 then proceeding as in Example 3, 8-benzyl-4H-pyrazolo[4',3':5,6]pyrido[3,4-e][1,2,4]triazolo[1,5-a]pyrimidin-5(8H)-one and 8-benzyl-4-(3-methylbutyl)-4H-pyrazolo[4',3':5,6]pyrido[3,4-e][1,2,4]triazolo[1,5-a]pyrimidin-5(8H)-one, respectively, are obtained.

EXAMPLE 21

4-Methyl-8-phenylethyl-2-propyl-4H-pyrazolo[4',3':5,6]pyrido[3,4-e][1,2,4]triazolo[1,5-a]pyrimidin-5(8H)-one By substituting 1-phenylethyl-4-hydrazino-1H-pyrazolo[3,4-b]pyridine-5-carboxylic acid, methyl ester for the 1-ethyl-4-hydrazino-1H-pyrazolo[3,4-b]pyridine-5-carboxylic acid, ethyl ester and 1-ethoxybutylidene cyanamide for the ethoxymethylene cyanamide in the procedure of Example 1, then proceeding as in Example 4, 2-propyl-8-phenylethyl-4H-pyrazolo[4',3':5,6-]pyrido[3,4-e][1,2,4]triazolo[1,5-a]pyrimidin-5(8H)-one and 4-methyl-8-phenylethyl-2-propyl-4H-pyrazolo[4',3':5,6]pyrido[3,4-e][1,2,4]triazolo[1,5-a]pyrimidin5(8H)-one, respectively, are obtained.

EXAMPLE 22

4,8-Diethyl-2-phenyl-4H-pyrazolo[4',3':5,6]pyrido[3,4-e][1,2,4]triazolo[1,5-a]pyrimidin-5(8H)-one By substituting α-ethoxybenzylidene cyanamide for the ethoxymethylene cyanamide in the procedure of Example 1, then proceeding as in Example 4 but substituting ethyl iodide for the methyl iodide, 8-ethyl-2-phenyl-4H-pyrazolo[4',3':5,6]pyrido[3,4-e][1,2,4]triazolo[1,5-a]pyrimidin-5(8H)-one and 4,8-diethyl-2-phenyl-4H-pyrazolo[4',3':5,6]pyrido[3,4-e][1,2,4]triazolo[1,5-a]-pyrimidin-5(8H)-one, respectively, are obtained.

EXAMPLE 23

4-Phenyl-4H-pyrazolo[4',3':5,6]pyrido[3,4-e][1,2,4]triazolo[1,5-a]pyrimidin-5(8H)-one

(a) 8-Furfuryl-4-phenyl-4H-pyrazolo[4',3':5,6]pyrido[3,4-e][1,2,4]triazolo[1,5-a]pyrimidin-5(8H)-one By substituting 4-hydrazino-1-furfurylpyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in Example 1, 8-furfuryl-4H-pyrazolo[4',3':5,6]pyrido[3,4-e][1,2,4]triazolo[1,5-a]pyrimidin-5(8H)-one is obtained. This compound is now processed as in Example 4, substituting bromobenzene for the methyl iodide. A small amount of copper catalyst is added to obtain 8-furfuryl-4-phenyl-4H-pyrazolo[4',3': 5,6]pyrido[3,4-e][1,2,4]triazolo[1,5-a]pyrimidin-5(8H)-one.

(b) 4-Phenyl-4H-pyrazolo[4',3':5,6]pyrido[3,4-e][1,2,4]-triazolo[1,5-a]pyrimidin-5(8H)-one 0.01 mol. of 1-furfuryl-4-phenyl-4H-pyrazolo[4',3':5,6]pyrido[3,4-e][1,2,4]triazolo[1,5-a]pyrimidin-5(8H)-one is heated in 50 ml. of diethyleneglycol dimethylether containing 0.01 mol. of selenium dioxide at reflux temperature with stirring for two hours. The mixture is filtered hot and evaporated to dryness. 4-Phenyl-4H-pyrazolo[4',3':5,6]pyrido[3,4-e][1,2,4]triazolo[1,5-a]-pyrimidin-5(8H)-one remains.

EXAMPLE 24

8-Benzoyl-4-phenyl-4H-pyrazolo[4',3':5,6]pyrido[3,4-e][1,2,4]triazolo[1,5-a]pyrimidin-5(8H)-one

0.01 mol. of 4-phenyl-4H-pyrazolo[4',3':5,6-]pyrido[3,4-e][1,2,4]triazolo[1,5-a]pyrimidin-5(8H)-one and 0.02 mol. of benzoyl chloride are stirred overnight in 50 ml. of dry pyridine at room temperature. On addition of 50 ml. of water, 8-benzoyl-4-phenyl-4H-pyrazolo[4',3':5,6]pyrido[3,4-e][1,2,4]-triazolo[1,5-a]pyrimidin-5(8H)-one is filtered off.

EXAMPLE 25

4-Methyl-8-(4-methylbenzoyl)-4H-pyrazolo[4',3':5,6-]pyrido[3,4-e][1,2,4]triazolo[1,5-a]pyrimidin-5(8H)-one

By substituting 1-(4-methylbenzoyl)-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, then proceeding as in Example 4, 8-(4-methylbenzoyl)-4H-pyrazolo[4',3':5,6]pyrido[3,4-e][1,2,4]triazolo[1,5-a]pyrimidin-5(8H)-one and 4-methyl-8-(4-methylbenzoyl)-4H-pyrazolo[4', 3':5,6]pyrido[3,4-e][1,2,4]triazolo[1,5-a]pyrimidine-5(8H)-one, respectively, are obtained.

EXAMPLE 26

4-(2-Aminoethyl)-6-methyl-8-ethyl-4H-pyrazolo[4',3':5,6]pyrido[3,4-e][1,2,4]triazolo[1,5-a]pyrimidin-5(8H)-one

By substituting the 8-ethyl-6-methyl-4H-pyrazolo[3',4':5,6]pyrido[3,4-e][1,2,4]triazolo[1,5-a]pyrimidin-5(8H)-one obtained in Example 19 in the procedure of Example 2 but substituting 2-chloroethylamine for the 3-(dimethylamino)propyl chloride, 4-(2-aminoethyl)-6-methyl-8-ethyl-4H-pyrazolo[4',3':5,6]pyrido[3,4-e][1,2,4]triazolo]1,5-a]pyrimidin-5(8H)-one is obtained.

EXAMPLE 27

4-(3-Ethoxypropyl)-8-ethyl-4H-pyrazolo[4',3':5,6-]pyrido[3,4-e][1,2,4]triazolo[1,5-a]pyrimidin-5(8H)-one

By substituting 3-ethoxypropyl chloride for the 3-(dimethylamino)propyl chloride in the procedure of Example 2 4-(3-ethoxypropyl)-8-ethyl-4H-pyrazolo[4',3':5,6]pyrido[3,4-e][1,2,4]triazolo[1,5-a]pyrimidin-5(8H)-one is obtained.

EXAMPLE 28

4-Methylthiomethyl-4H-pyrazolo4',3':5,6]pyrido[3,4-e][1,2,4]-triazolo[1,5-a]pyrimidin-5(8H)-one

By substituting methylthiomethyl chloride for the 3-(dimethylamino)propyl chloride in the procedure of Example 2 and substituting the 4H-pyrazolo[1,5-a]pyrazolo[4',3':5,6]pyrido[3,4-e][1,2,4]triazolo[1,5-a]pyrimidin-5(8H)-one obtained in Example 11 for the 8-ethyl-4H-pyrazolo[4',3':5,6]pyrido[3,4-e][1,2,4]triazolo[1,5-a]pyrimidin-5(8H)-one, 4-methylthiomethyl-4H-pyrazolo[4',3':5,6]pyrido[3,4-e][1,2,4]-triazolo[1,5-a]pyrimidin-5(8H)-one is obtained.

EXAMPLE 29

8-Benzoyl-4-(p-methylphenyl)-4H-pyrazolo[4',3':5,6-]pyrido[3,4-e][1,2,4]triazolo[1,5-a]pyrimidin-5(8H)-one

By substituting p-methylphenyl bromide for the bromobenzene in the procedure of Example 23a, then proceeding as in part b and Example 24, 4-(p-methyphenyl)-4H-pyrazolo[4',3':5,6]pyrido[3,4-e][1,2,4]triazolo[1,5-a]pyrimidin-5(8H)-one and 8-benzoyl-4-(p-methylphenyl)-4H-pyrazolo[4',3':5,6-]pyrido[3,4-e][1,2,4]triazolo[1,5-a]pyrimidin-5(8H)-one, respectively, are obtained.

EXAMPLE 30

4-[2-Diethylamino(ethyl)]-8,10-dimethyl-4H-pyrazolo-[4',3':5,6]pyrido[3,4-e][1,2,4]triazolo[1,5-a]pyrimidin-5(8H)-one

By substituting diethylaminoethyl chloride for the 3-(dimethylamino)propyl chloride and utilizing the 8,10-dimethyl-4H-pyrazolo[4',3':5,6]pyrido[3,4-e][1,2,4]triazolo[1,5-a]pyrimidin-5(8H)-one product of Example 15 instead of 8-ethyl-4H-pyrazolo[4',3':5,6-]pyrido[3,4-e][1,2,4]triazolo[1,5-a]pyrimidin-5(8H)-one in the procedure of Example 2, 4-[2-(dimethylamino)ethyl]-8,10-dimethyl-4H-pyrazolo[4',3'-5,6]pyrido[3,4-e][1,2,4]triazolo[1,5-a]pyrimidin-5(8H)-one is obtained.

EXAMPLE 31

4-Dimethylaminomethyl-8-phenyl-4H-pyrazolo[4',3':5,6]pyrido[3,4-e][1,2,4]triazolo[1,5-a]pyrimidin-5(8H)-one

By substituting dimethylaminomethyl chloride for the 3-(dimethylamino)propyl chloride in the procedure of Example 2 and utilizing 8-phenyl-4H-pyrazolo-[4',3':5,6]pyrido[3,4-e][1,2,4]triazolo[1,5-a]pyrimidin-5(8H)-one product of Example 18 instead of 8-ethyl-4H-pyrazolo[4',3':5,6]pyrido[3,4-e][1,2,4]triazolo[1,5-a]pyrimidin-5(8H)-one, 4-dimethylaminomethyl-8-phenyl-4H-pyrazolo[4',3':5,6]pyrido[3,4-e][1,2,4]triazolo[1,5-a]pyrimidin-5(8H)-one is obtained.

EXAMPLE 32

8-Ethyl-4-(2-thiamorpholino)ethyl-4H-pyrazolo[4',3':5,6]pyrido[3,4-e][1,2,4]triazolo[1,5-a]pyrimidin-5(8H)-one By substituting 1-chloro-2-thriamorpholinoethane for the 1-chloro-2-morpholinoethane in the procedure of Example 8, 8-ethyl-4-(2-thiamorpholino)ethyl-4H-pyrazolo[4',3':5,6]pyrido[3,4-e][1,2,4]triazolo[1,5-a]pyrimidin-5(8H)-one is obtained.

EXAMPLE 33

4-(3-Piperazino)propyl-4H-pyrazolo[4',3':5,6-]pyrido[3,4-e][1,2,4]triazolo[1,5-a]pyrimidin-5(8H)-one By substituting 3-piperazinopropyl chloride for the 1-chloro-2-morpholinoethane in the procedure of Example 8 and utilizing the 4H-pyrazolo[4',3':5,6-]pyrido[3,4-e][1,2,4]triazolo[1,5-a]pyrimidin-5(8H)-one product of Example 11, 4-(3-piperazino)propyl-4H-pyrazolo[4',3':5,6]pyrido[3,4-e][1,2,4]triazolo[1,5-a]pyrimidin-5(8H)-one is obtained.

EXAMPLE 34

The following ingredients are used to make 1,000 200 mg. tablets each containing 100 mg. of active ingredient:

| | |
|---|---|
| 8-ethyl-4H-pyrazolo [4', 3':5,6] pyrido-[3,4-e] [1,2,4] triazolo [1,5-a] pyrimidine-5 (8H)-one | 100 gm. |
| Polyvinyl pyrrolidone | 7.5 gm. |
| Lactose | 20 gm. |
| Magnesium stearate | 3.5 gm. |
| Corn starch | 17.5 gm. |
| Avicel (microcrystalline cellulose) | 51.5 gm. |

The medicament and lactose are thoroughly admixed. The polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray pan.

What is claimed is:

1. A compound of the formula

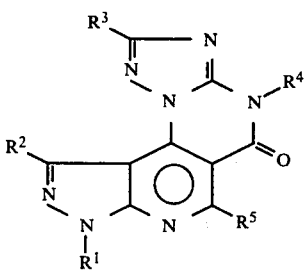

wherein $R^1$ is hydrogen, lower alkyl, phenyl, phenyl-lower alkylene, $R_8$-benzoyl;

$R^2$ and $R^5$ each is hydrogen or lower alkyl;

$R^3$ is hydrogen, lower alkyl, phenyl, lower alkylthio or lower alkylsulfinyl;

$R^4$ is hydrogen, lower alkyl, phenyl-lower alkylene, $R_8$-benzoyl, lower alkanoyl, lower alkoxy-lower alkylene, lower alkylthio-lower alkylene, $R_8$-phenyl, amino-lower alkylene or

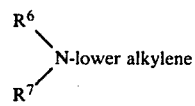

wherein $R^6$ and $R^7$ each is lower alkyl or together join to complete the heterocycle piperidine, morpholine, thiamorpholine or piperazine;

$R_8$ is hydrogen, halogen, lower alkoxy or lower alkyl; said lower alkyl, lower alkylene, lower alkoxy and lower alkanoyl groups having up to seven carbon atoms.

2. A compound as in claim 1 wherein $R^1$ is lower alkyl; $R^2$ and $R^5$ each is hydrogen or lower alkyl; $R^3$ is hydrogen, lower alkyl, lower alkylthio or lower alkylsulfinyl; and $R^4$ is hydrogen, lower alkyl or di-lower alkylamino-lower alkylene.

3. A compound as in claim 1 wherein $R^1$ is lower alkyl, $R^2$, $R^3$ and $R^5$ each is hydrogen or lower alkyl; and $R^4$ is hydrogen, lower alkyl or di-lower alkylamino-lower alkylene.

4. A compound as in claim 3 wherein the lower alkyl and lower alkylene groups have up to 4 carbon atoms.

5. A compound as in claim 1 wherein $R^4$ is lower alkyl.

6. A compound as in claim 1 wherein $R^4$ is di-lower alkylamino-lower alkylene.

7. A compound as in claim 1 wherein $R^3$ is lower alkylthio.

8. A compound as in claim 1 wherein $R^3$ is lower alkylsulfinyl.

9. A compound as in claim 1 wherein $R^1$ and $R^4$ each is lower alkyl and $R^2$, $R^3$ and $R^5$ each is hydrogen.

10. A compound as in claim 1 wherein $R^2$, $R^3$ and $R^5$ each is hydrogen.

11. A compound as in claim 10 wherein $R^1$ is ethyl and $R^4$ is hydrogen.

12. A compound as in claim 10 wherein $R^1$ is ethyl and $R^4$ is isopentyl.

13. A compound as in claim 10 wherein $R^1$ is ethyl and $R^4$ is 3-dimethylaminopropyl.

14. A compound as in claim 10 wherein $R^1$ is ethyl and $R^4$ is methyl.

15. A compound as in claim 1 wherein $R^1$ is ethyl, $R^2$, $R^4$ and $R^5$ each is hydrogen and $R^3$ is methylthio.

16. A compound as in claim 1 wherein $R^1$ is ethyl, $R^2$, $R^4$ and $R^5$ each is hydrogen and $R^3$ is methylsulfinyl.

17. A composition comprising about 10 to 250 mg. of a compound of claim 1 and a physiologically acceptable carrier therefor.

18. A method for treating inflammation which comprises administering to a mammal suffering therefrom a composition comprising about 10 to 250 mg. of a compound of claim 1 and a physiologically acceptable carrier therefor.

* * * * *

UNITED STATES PATENT OFFICE
CERTIFICATE OF CORRECTION

PATENT NO. : 4,269,836
DATED : May 26, 1981
INVENTOR(S) : Theodor Denzel, Hans Hoehn It is certified that error appears in the above-identified patent and that said Letters Patent are hereby corrected as shown below:

Col. 2, formula II, the right hand portion of the formula should read

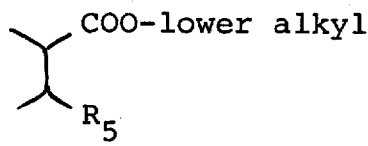

Col. 5, line 31, after 8 should be inserted a hyphen ( - ).
Col. 5, line 40, after pyridine should be inserted a hyphen ( - ).
Col. 5, line 44, after 4H should be inserted a hyphen ( - ).
Col. 5, line 69, "4,8-dimethyl-" should be -- 4,8-diethyl- --.
Col. 6, line 13, "morphoninoethane" should be
-- morpholinoethane -- .
Col. 6, line 14, "precipitte" should be -- precipitate -- .
Col. 7, line 6, after 4 (first occurrence) should be inserted a hyphen ( - ). Col. 10, line 15, after pyrazolo should be inserted a bracket -- [ -- .
Col. 11, line 7, "thriamorpholinoethane" should be
-- thiamorpholinoethane --.

Signed and Sealed this

Seventh Day of February 1984

[SEAL]

Attest:

GERALD J. MOSSINGHOFF

Attesting Officer   Commissioner of Patents and Trademarks